United States Patent [19]

Kleemann et al.

[11] 4,345,072

[45] Aug. 17, 1982

[54] PROCESS FOR THE PRODUCTION OF 5-ARYLIDENE HYDANTOINS (B)

[75] Inventors: Axel Kleemann, Hanau; Theodor Lussling, Constance; Wolf Pfeifer, Bruhl; Paul Scherberich, Constance, all of Fed. Rep. of Germany

[73] Assignee: Degussa AG, Frankfurt, Fed. Rep. of Germany

[21] Appl. No.: 251,540

[22] Filed: Apr. 6, 1981

[30] Foreign Application Priority Data

Apr. 9, 1980 [DE] Fed. Rep. of Germany ....... 3013647

[51] Int. Cl.³ .................. C07D 233/72; C07D 233/76
[52] U.S. Cl. .................................. 542/442; 542/429; 542/445
[58] Field of Search ........................ 542/442, 445, 429

[56] References Cited

U.S. PATENT DOCUMENTS 2,861,079 11/1958 Britton et al. ...................... 542/442
3,321,470 5/1967 Howell et al. ...................... 542/442
4,241,073 12/1980 Jamieson et al. ................... 542/442

OTHER PUBLICATIONS

Thielemann; Sci. Pharm. 39, (1971), p. 815.
Thielemann; Wiss 2 Univ. Halle, XX, 1971, M, H, S, 89–95.
Wheeler e.a. Amer. J. Chem. 45 (1911), pp. 368–383.
Thielemann (B) Chem. Abst. 75 (1971), #5638.
Thielemann e. a. (A) Chem. Abst. 76 (1972), #153669.
Phillips J. Org. Chem. 16 (1951), pp. 954–962.

Primary Examiner—Arthur P. Demers
Attorney, Agent, or Firm—Cushman, Darby & Cushman

[57] ABSTRACT

5-Arylidene hydantoins are produced by condensation of an aromatic aldehyde with hydantoin in the presence of at least one ammonium salt of an aliphatic or aromatic carboxylic acid. The desired 5-arylidene hydantoins are obtained in high yields.

14 Claims, No Drawings

PROCESS FOR THE PRODUCTION OF 5-ARYLIDENE HYDANTOINS (B)

BACKGROUND OF THE INVENTION

The object of the invention is the development of a process for the production of 5-arylidene hydantoins substituted or unsubstituted in the aromatic nucleus by condensation of the corresponding substituted or unsubstituted aromatic aldehyde with hydantoin in the presence of a carboxylic acid.

5-arylidene hydantoins are important intermediate products for the production of phenylalanine and phenylalanines substituted in the aromatic nucleus.

It is already known to produce 5-arylidene hydantoins by condensation of benzaldehyde or substituted aromatic aldehydes with hydantoin in the presence of acetic acid and anhydrous sodium acetate (Wheeler and Hoffmann, Amer. Chem. J. Volume 45, pages 368–383 (1911)). In the reaction of benzaldehyde, the yields, for example, are 70 to 80% based on the hydantoin employed. However, to produce these yields, there is required the use of relatively large amounts of anhydrous sodium.

SUMMARY OF THE INVENTION

The process of the invention is characterized by condensing an aromatic aldehyde with hydantoin in the presence of at least one ammonium salt of an aliphatic or aromatic carboxylic acid.

The process of the invention already even with addition of relatively small amounts of ammonium salt surprisingly gives higher yields of the desired 5-arylidene hydantoin.

The process of the invention is particularly suited for the production of 5-arylidene hydantoins of the general formula

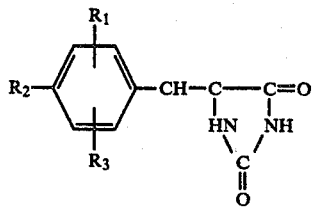

in which $R_1$, $R_2$, and $R_3$ are the same or different and in each case is hydrogen, halogen, e.g., of atomic weight 9 to 80, a hydroxy group, a nitro group, an amino group, an unbranched or branched alkyl or alkenyl group, a cycloalkyl group, a cycloalkenyl group, an aryl group, an aralkyl group, a alkaryl group, an alkylthio group, an acyloxy group, an acylthio group, a mono or dialkylamino group, or an acylamine group. Preferably, the alkyl groups contain 1 to 6, especially 1 to 3, carbon atoms, the alkenyl group 2 to 6, especially 2 to 3, carbon atoms, the cycloalkyl and cycloalkenyl groups 3 to 8, preferably 3 to 6 carbon atoms. In a given case in the cycloalkyl or cycloalkenyl group, one or more —CH$_2$— units can also be replaced by —O—, —S—, or —NH— or —CH= by —N— so that there is present the corresponding heterocylic ring with 3 to 8, especially 3 to 6 ring members. Preferably, the aralkyl and the alkaryl groups contain 1 to 6, especially 1 to 3, carbon atoms in the alkylene or alkyl groups. The alkoxy, alkylthio, acyloxy, acylthio, monomer dialkylamino and acylamino groups contain preferably 1 to 6, especially 1 to 3, carbon atoms in the alkyl or acyl groups. In a given case, two of the groups $R_1$ to $R_3$ together can also form an alkylene or alkenylene group with 1 to 6, especially 1 to 4, carbon atoms, whereby in this case also one or more —CH$_2$ can be replaced by —O—, —S— or —NH— or —CH= by —N=.

Accordingly, there are employed aromatic aldehydes of the general formula

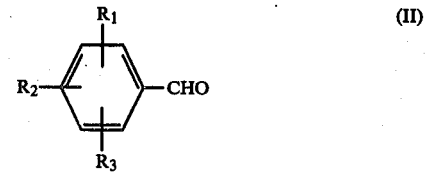

in which $R_1$, $R_2$, and $R_3$ are as defined above. Such aldehydes include, for example, benzaldehyde, tolylaldehyde, 4-isopropylbenzaldehyde, 4-hydroxybenzaldehydehyde, 3,4,5-trimethoxybenzaldehyde, 3-bromo-4-methoxybenzaldehyde, 3,4-methylenedioxybenzaldehyde, 2-hydroxy-4-nitrobenzaldehyde, 4,5-dimethoxy-2-nitrobenzaldehyde, salicyaldehyde, vanillin, 4-phenylbenzaldehyde, 4-benzylbenzaldehyde, 4-fluorobenzaldehyde, 4-dimethylaminobenzaldehyde, 4-acetoxybenzaldehyde, 4-acetaminobenzaldehyde, 4-methylthiobenzaldehyde, and 3,5-dichloro-4-hydroxybenzaldehyde. Additional aldehydes include p-tolylaldehyde, m-tolyaldehyde, 4-chlorobenzaldehyde, 4-hexylbenzaldehyde, 2-allylbenzaldehyde, 4-allylbenzaldehyde, 2-vinylbenzaldehyde, 3-vinylbenzaldehyde, 4-methallylbenzaldehyde, 4-crotylbenzaldehyde, 2-nitrobenzaldehyde, 3-nitrobenzaldehyde, 4-nitrobenzaldehyde, 2-aminobenzaldehyde, 4-aminobenzaldehyde, 4-cyclopropylbenzaldehyde, 2-cyclopropylbenzaldehyde, 4-cyclohexylbenzaldehyde, 2,6-dichlorobenzaldehyde, anisaldehyde, 3-hydroxybenzaldehyde, 2-hydroxybenzaldehyde, 2-hydroxy-4-methylbenzaldehyde, 2-hydroxy-3-methoxybenzaldehyde, veratraldehyde, 2,4-dihydroxybenzaldehyde, 2,5-dihydroxybenzaldehyde, 4-cyclohexenylbenzaldehyde, 4-cyclooctylbenzaldehyde, 4-piperidinylbenzaldehyde, 4-pyridinebenzaldehyde, 4-furylbenzaldehyde, 4-thienylbenzaldehyde, 4-phenylethylbenzaldehyde, 4-sec.butylbenzaldehyde, 4-morpholinobenzaldehyde, 4-isopropoxybenzaldehyde, 2-propoxybenzaldehyde, 3-ethoxybenzaldehyde, 4-hexoxybenzaldehyde, 2-isopropylaminobenzaldehyde, 4-hexylaminobenzaldehyde, 4-diethylaminobenzaldehyde, 4-dipropylaminobenzaldehyde, 4-methylethylaminobenzaldehyde, 3,4-ethylenedioxybenzaldehyde, 4-acethiobenzaldehyde, 4-propionoxybenzaldehyde, 4-formoxybenzaldehyde, 4-butyroxybenzaldehyde, 3,4-tetramethylenebenzaldehyde, 3,4-trimethylenebenzaldehyde.

The condensation with the hydantoin takes places in the presence of an ammonium salt of an aliphatic or aromatic carboxylic acid. Suitable carboxylic acids, for example, are alkanoic acids such as formic acid, acetic acid, propionic acid, butyric acid, 2-methylbutyric acid, valeric acid, isovaleric acid, caproic acid, 2-chloroacetic acid, 2-bromoacetic acid, dichloroacetic acid, trichloroacetic acid, capric acid, 2-hydroxyacetic acid, benzoic acid, mandelic acid, phenylacetic acid, cinnamic acid, phenylpropronic acid, crotonic acid, fumaric acid, acetic acid, citric acid, lactic acid, tartaric acid. There can be used ammonium salts of mixtures of such carboxylic acids.

The ammonium salt can be added as such or can be produced in the reaction mixture from the carboxylic acid concerned and ammonia. It can be advantageous to carry out the condensation in a solvent. As such, there can be used excess carboxylic acid, water, aliphatic or aromatic alcohols, aliphatic or aromatic ethers, aliphatic or aromatic hydrocarbons, halogenated aliphatic or aromatic hydrocarbons and their mixtures. Examples of solvents which can be employed include n-butanol, t-butanol, toluene, benzyl alcohol, xylene, or chlorobenzene and their mixtures as well as n-hexanol, methanol, ethanol, propanol, isopropanol, diethyl ether, dipropyl ether, dibutyl ether, hexane, octane, ligroin, benzene, trichloroethylene, dichloroethane, methyl phenyl ether, diphenyl ether.

Generally, the condensation takes place at a temperature between about 80° and 200° C., especially at a temperature between 100° C. and the boiling temperature of the mixture. The pressure can be chosen substantially at random. Thus, operation can be at normal pressure as well as at lower or higher pressure. Although it is generally advantageous to operate at about normal pressure, because of the volatility of the materials elevated pressure can be required.

The molar ratio of aldehyde to hydantoin can be either stoichiometric or under or over stoichiometric. Generally, it is advantageous to employ per mole of hydantoin about 1 to 2 moles, especially 1.2 to 1.5 moles of the aldehyde.

Per mole of hydantoin, there is suitably employed at least 0.2 mole, preferably 0.5 to 2.0 moles, especially 0.8 to 1.2 moles of ammonium salt.

Furthermore, it can be advantageous to separate off the water formed during the reaction by distillation.

The process can comprise, consist essentially of, or consist of the steps set forth with the stated materials.

EXAMPLE 1

A mixture of 100 grams (1.0 mole) of hydantoin, 117 grams (1.1 moles) of benzaldehyde, 77 grams (1.0 mole) of ammonium acetate, and 240 grams (4.0 moles) of acetic acid were held for 4 hours at reflux temperature. In the cooling to room temperature, the 5-benzylidene hydantoin separated out. The yield was 179 grams, corresponding to 95% of theory based on hydantoin. The product had a melting point of 219°–220° C. and was homogeneous as was established by thin layer chromatography.

COMPARISON EXAMPLE 1

The procedure was as in accordance with Example 1; but in place of ammonium acetate, there were employed 82 grams (1.0 mole) of sodium acetate. There were obtained 86.5 grams of 5-benzylidene hydantoin corresponding to 46% of theory based on hydantoin.

COMPARISON EXAMPLE 2

The procedure was as in Example 1; but in place of ammonium acetate, there were employed 98 grams (1.0 mole) of potassium acetate. There were obtained 79 grams of 5-benzylidene hydantoin corresponding to a yield of 42% of theory based on hydantoin.

EXAMPLE 2

A mixture of 100 grams (1.0 mole) of hydantoin, 106 grams (1.0 mole) of benzaldehyde, 63 grams (1.0 mole) of ammonium formate, and 230 grams (5.0 moles) of formic acid were held for 3 hours at reflux temperature. After the cooling off, there were obtained 173 grams of 5-benzylidene hydantoin, corresponding to 92% of theory based on hydantoin.

EXAMPLE 3

To a mixture of 100 grams (1.0 mole) of hydantoin, 106 grams (1.0 mole) of benzaldehyde, and 370 grams (5.0 moles) of propionic acid, there were added 17 grams (1.0 mole) of ammonia. The mixture was subsequently held for 3 hours at reflux temperature. After the cooling off, there were obtained 178 grams of 5-benzylidene hydantoin, corresponding to 95% of theory based on hydantoin.

EXAMPLE 4

A mixture of 100 grams (1.0 mole) of hydantoin, 151 grams (1.0 mole) of 4-nitrobenzaldehyde, 77 grams (1.0 mole) of ammonium acetate, 120 grams (2.0 moles) of acetic acid, and 200 ml of n-butanol were held for 3 hours at reflux temperature. After the cooling, there were obtained 219 grams of 5-(4'-nitrobenzylidene)-hydantoin, corresponding to 94% of the theory based on hydantoin. The product had a melting point of 253°–254° C. and homogeneous by thin layer chromatography.

EXAMPLE 5

The procedure was as in Example 1, but there were employed 119 grams (1.1 moles) of 4-methoxybenzaldehyde. The yield of 5-(4'methoxybenzylidene)-hydantoin was 207 grams, corresponding to 95% of theory based on hydantoin. The product had a melting point of 243°–244° C.

EXAMPLE 6

The procedure was as in Example 1, but there were employed 169 grams (1.2 moles) of 2-chlorobenzaldehyde. The yield of 5-(2'-chlorobenzylidene)-hydantoin was 200 grams, corresponding to 90% of theory, based on hydantoin.

EXAMPLE 7

The procedure was as in Example 1, but there were employed 150 grams (1.0 mole) of 3,4-methylenedioxybenzaldehyde. The yield of 5-(3',4'-methylenedioxybenzylidene)-hydantoin was 207 grams, corresponding to 89% of theory based on hydantoin.

EXAMPLE 8

The procedure was as in Example 1, but there were employed 122 grams (1.0 mole) of 4-hydroxybenzaldehyde. The yield of 5-(4'-hydroxybenzylidene)-hydantoin was 184 grams, corresponding to 90% of theory based on the hydantoin. The product had a melting point of 314°–316° C. and was homogeneous by thin layer chromatography.

What is claimed is:

1. In a process for the production of a 5-arylidene hydantoin which is substituted or unsubstituted in the aromatic nucleus by condensation of the corresponding substituted or unsubstituted aromatic aldehyde with hydantoin the improvement comprising carrying out the condensation in the presence of at least one ammonium salt of an aliphatic or aromatic carboxylic acid.

2. A process according to claim 1 wherein there is employed at least 0.2 mole of the ammonium salt per mole of reacting hydantoin.

3. A process according to claim 2 wherein there is employed 0.5 to 2.0 moles of ammonium salt per mole of the hydantoin.

4. A process according to claim 2 wherein the temperature is 80° to 200° C.

5. A process according to claim 4 wherein the ammonium salt is a salt of a carboxylic acid which is an alkanoic acid, a haloalkanoic acid, a hydroxyalkanoic acid, an alkenoic acid, aryl carboxylic acid, phenyl alkanoic acid, phenyl hydroxyalkanoic acid, or phenyl alkenoic acid.

6. A process according to claim 2 wherein the arylidene hydantoin formed has the formula

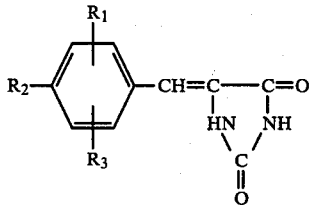

and the aldehyde employed has the formula

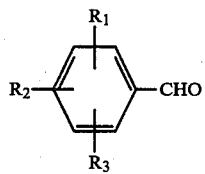

where $R_1$, $R_2$, and $R_3$ are hydrogen, alkyl, alkenyl, cycloalkyl, cycloalkenyl, aryl, halogen, hydroxy, nitro, amino, alkylamino, dialkylamino, alkoxy, alkylthio, acyloxy, acylthio, alkaryl, aralkyl, acylamino, cycloalkyl having a —$CH_2$— group replaced by —O—, —S—, or —NH—, cycloalkenyl having a —CH— replaced by —N— or where two of the members $R_1$, $R_2$, and $R_3$ are joined together to forma an alkylene group or an alkenylene group or an alkylene group having at least one —$CH_2$— group replaced by —O—, —S—, or —NH— or an alkenylene group having at least one —CH= group replaced by —N=.

7. A process according to claim 6 wherein the aldehyde employed is benzaldehyde, tolylaldehyde, 4-isopropylbenzaldehyde, 4-hydroxybenzaldehyde, 3,4,5-trimethoxybenzaldehyde, 3-bromo-4-methoxybenzaldehyde, 3,4-methylenedioxybenzaldehyde, 2-hydroxy-4-nitrobenzaldehyde, 4,5-dimethoxy-2-nitrobenzaldehyde, salicyaldehyde, vanillin, 4-phenylbenzaldehyde, 4-benzylbenzaldehyde, 4-fluorobenzaldehyde, 4-dimethylaminobenzaldehyde, 4-acetoxybenzaldehyde, 4-acetaminobenzaldehyde, 4-methylthiobenzaldehyde, 3,5-dichloro-4-hydroxybenzaldehyde, p-tolylaldehyde, m-tolylaldehyde, 4-chlorobenzaldehyde, 4-hexylbenzaldehyde, 2-allylbenzaldehyde, 4-allylbenzaldehyde, 2-binylbenzaldehyde, 3-vinylbenzaldehyde, 4-methallylbenzaldehyde, 4-crotylbenzaldehyde, 2-nitrobenzaldehyde, 3-nitrobenzaldehyde, 4-nitrobenzaldehyde, 2-aminobenzaldehyde, 4-aminobenzaldehyde, 4-cyclopropylbenzaldehyde, 2-cyclopropylbenzaldehyde, 4-cyclohexylbenzaldehyde, 2,6-dichlorobenzaldehyde, anisaldehyde, 3-hydroxybenzaldehyde, 2-hydroxybenzaldehyde, 2-hydroxy-4-methylbenzaldehyde, 2-hydroxy-3-methoxybenzaldehyde, veratraldehyde, 2,4-dihydroxybenzaldehyde, 2,5-dihydroxybenzaldehyde, 4-cyclohexenylbenzaldehyde, 4-cyclooctylbenzaldehyde, 4-piperidinylbenzaldehyde, 4-pyridinobenzaldehyde, 4-furylbenzaldehyde, 4-thienylbenzaldehyde, 4-phenylethylbenzaldehyde, 4-phenylpropylbenzaldehyde, 4-ethylbenzaldehyde, 4-sec.butylbenzaldehyde, 4-morpholinobenzaldehyde, 4-isopropoxybenzaldehyde, 2-propoxybenzaldehyde, 3-ethoxybenzaldehyde, 4-hexoxybenzaldehyde, 4-propionaminobenzaldehyde, benzaldehyde-4-foramide, 4-propylthiobenzaldehyde, 3-methylaminobenzaldehyde, 2-isopropylaminobenzaldehyde, 4-hexylaminobenzaldehyde, 4-methylethylaminobenzaldehyde, 3,4-ethylenedioxybenzaldehyde, 4-acethiobenzaldehyde, 4-propionoxybenzaldehyde, 4-formoxybenzaldehyde, 4-butyroxybenzaldehyde, 3,4-tetramethylenebenzaldehyde, and 3,4-trimethylenebenzaldehyde.

8. A process according to claim 7 wherein the aldehyde employed is benzaldehyde, 4-nitrobenzaldehyde, 4-methoxybenzaldehyde, 2-chlorobenzaldehyde, 3,4-methylenedioxybenzaldehyde, or 4-hydroxybenzaldehyde.

9. A process according to claim 8 wherein the aldehyde employed is benzaldehyde.

10. A process according to claim 8 wherein the aldehyde employed is 4-nitrobenzaldehyde.

11. A process according to claim 8 wherein the aldehyde employed is 4-methoxybenzaldehyde.

12. A process according to claim 8 wherein the aldehyde employed is 2-chlorobenzaldehyde.

13. A process according to claim 8 wherein the aldehyde employed is 3,4-methylenedioxybenzaldehyde.

14. A process according to claim 8 wherein the aldehyde employed is 4-hydroxybenzaldehyde.

* * * * *